United States Patent
Lorenz et al.

(10) Patent No.: US 9,867,586 B2
(45) Date of Patent: Jan. 16, 2018

(54) STEREO X-RAY TUBE BASED SUPPRESSION OF OUTSIDE BODY HIGH CONTRAST OBJECTS

(71) Applicant: KONINKLIJKE PHILIPS N.V., Eindhoven (NL)

(72) Inventors: Cristian Lorenz, Hamburg (DE); Michael Grass, Buchholz in der Nordheide (DE); Dirk Schäfer, Hamburg (DE); Bernhard Johannes Brendel, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 418 days.

(21) Appl. No.: 14/383,127

(22) PCT Filed: Mar. 4, 2013

(86) PCT No.: PCT/IB2013/051699
§ 371 (c)(1),
(2) Date: Sep. 5, 2014

(87) PCT Pub. No.: WO2013/132407
PCT Pub. Date: Sep. 12, 2013

(65) Prior Publication Data
US 2015/0023471 A1    Jan. 22, 2015

Related U.S. Application Data

(60) Provisional application No. 61/607,040, filed on Mar. 6, 2012.

(51) Int. Cl.
*A61B 6/03* (2006.01)
*A61B 6/00* (2006.01)
(Continued)

(52) U.S. Cl.
CPC .............. *A61B 6/5252* (2013.01); *A61B 6/03* (2013.01); *A61B 6/4021* (2013.01);
(Continued)

(58) Field of Classification Search
CPC ......... A61B 6/022; A61B 6/025; A61B 6/466; A61B 6/469; A61B 6/5252; A61B 6/5294; G06T 7/0075
See application file for complete search history.

(56) References Cited

U.S. PATENT DOCUMENTS

| | | |
|---|---|---|
| 2009/0087026 A1 | 4/2009 | Xie et al. |
| 2011/0107270 A1 | 5/2011 | Wang et al. |
| 2012/0257810 A1 | 10/2012 | Von Berg et al. |

FOREIGN PATENT DOCUMENTS

| | | |
|---|---|---|
| JP | 8210847 A | 8/1996 |
| JP | 10051813 A | 2/1998 |

(Continued)

OTHER PUBLICATIONS

Dong et al, "Processing X-Ray Images to Eliminate Irrelevant Structures That Mask Important Features", vol. 28, No. 6, Sep. 2004, pp. 321-331.

(Continued)

*Primary Examiner* — Thomas R Artman

(57) ABSTRACT

A double focal spot X-ray tube is used to acquire a set of two images PIα, PIβ for a given gantry position from slightly different view positions. The stereo or binocular disparity (BD) of imaged structures is used to estimate the object depth in view direction, which in turn is used to discriminate between objects inside IO and outside EO the body. Respective structures are virtually removed from the images PIα, PIβ.

18 Claims, 4 Drawing Sheets

(51) Int. Cl.
　　　*G06T 5/00*　　　(2006.01)
　　　*G06T 15/00*　　(2011.01)
　　　*G06T 7/593*　　 (2017.01)

(52) U.S. Cl.
　　　CPC .......... *A61B 6/4441* (2013.01); *A61B 6/5235* (2013.01); *A61B 6/5258* (2013.01); *G06T 5/00* (2013.01); *G06T 7/593* (2017.01); *G06T 15/00* (2013.01); *G06T 2207/10116* (2013.01); *G06T 2207/20172* (2013.01); *G06T 2207/30004* (2013.01)

(56) References Cited

FOREIGN PATENT DOCUMENTS

| | | | |
|---|---|---|---|
| JP | 10094539 A | 4/1998 | |
| JP | 11351862 A | 12/1999 | |
| WO | 2011077334 A1 | 6/2011 | |

OTHER PUBLICATIONS

Dobbins et al, "Chest Tomosynthesis: Technical Principles and Clinical Update", European Journal of Radiology, vol. 72, No. 2, Nov. 2009, pp. 244-251.

Jun et al, "Digital Tomosynthesis Mammography: Improvement of Artifact Reuction Emthod for High-Attenuation Objects on Reconstructed Slices", Proceedings of SPIE, vol. 6913, Mar. 6, 2008, pp. 691340-691340-6.

Hamarneh, G., "N-Sift: N-Dimensional Scale Invariant Feature Transform", IEEE Transactions on Image Processing, vol. 18, pp. 2012-2021, Sep. 2009.

STEREO X-RAY TUBE BASED SUPPRESSION OF OUTSIDE BODY HIGH CONTRAST OBJECTS

CROSS-REFERENCE TO PRIOR APPLICATIONS

This application is the U.S. National Phase application under 35 U.S.C. §371 of International Application Serial No. PCT/IB2013/051699, filed on Mar. 4, 2013, which claims the benefit of U.S. Application Ser. No. 61/607,040, filed on Mar. 6, 2012. These applications are hereby incorporated by reference herein.

FIELD OF THE INVENTION

The present invention relates to an image processing apparatus, to a method of image processing, to an imaging system, to a computer program element, and to a computer readable medium.

BACKGROUND OF THE INVENTION

In interventional imaging settings, cables, electronic devices and sundry equipment are often located outside a patient's body and frequently create spurious image content in intra-interventional imaging. This image content originating from instrumentation or other devices outside the body can be visually disturbing, in particular in time-critical settings.

SUMMARY OF THE INVENTION

There may therefore be a need for an image processing apparatus to support a clinician during imaging.

The object of the present invention is solved by the subject matter of the independent claims wherein further embodiments are incorporated in the dependent claims.

It should be noted that the following described aspects of the invention equally apply to the method of image processing, to the imaging system, to the computer program element and to the computer readable medium.

According to one aspect of the present invention there is provided an image processing apparatus comprising:

an input interface unit for receiving at least two projection images of a subject taken at different projection angles by an X-ray scanner, each of the images including a footprint of a target object;

an image depth resolver configured to use the two image footprints to determine whether the target object was external to the subject when the images were taken;

an image manipulator configured to replace at least a portion of the image footprint in at least one of the images by different image information when the target object is determined by the resolver to be external, an output interface unit configured to output the so manipulated image.

The apparatus proposed herein uses the stereo or binocular disparity of image content to estimate the depth of the respective structure. This allows distinguishing between structures inside and outside the body. Image content originating from objects outside the body is removed from the image. The so processed image then affords when viewed a substantially un-obscured clear view on the clinically interesting anatomical structures.

In other words, the apparatus implements stereo X-ray tube based suppression of outside body objects. In one embodiment it is the high contrast or high attenuation objects that are suppressed.

According to one embodiment, the image depth resolver is configured to establish the binocular disparity between the two target object footprints and to compare the established binocular disparity with a user definable disparity threshold value to determine whether the target object is external.

According to one embodiment, the binocular disparity threshold value is adjustable in response to a user input, the value correlating to an expected or measured thickness of the subject.

According to one embodiment, the image manipulator is configured to replace the image footprint by image information interpolated from at least part of the image information forming the remainder of the at least one image.

According to one embodiment, the apparatus further comprises an object footprint detector configured to detect the footprint in at least one of the two images.

According to one embodiment, the image depth resolver is arranged to receive input on the footprint by the object footprint detector, the detector configured to provide the input on the detected objet footprint to the image depth resolver only if the detected object footprint matches one or more selection criteria.

According to one embodiment, the selection criteria include any one or a combination of shape and X-ray opacity or attenuation profile.

According to one embodiment, the object footprint detector is configured to by-pass/leapfrog the image depth resolver if, based on the used criteria, the object is a priori determined to be external. This affords saving CPU time in cases where object recognition allows unambiguously to conclude that the relevant shape originates from an external object.

The apparatus may be used in X-ray applications where two projection images acquired at nearly identical views are available. The apparatus may be used in situations such as interventional X-ray, emergency setting or other time-critical applications where disturbing image content occurs that is caused by outside patient objects.

According to one embodiment, once enabled by the medical professional during or before us of the imager, operation of the image processor automatically resumes once images have been acquired. Operation of image processor can be enabled or disabled as desired during the imaging session.

According to another aspect of the invention there is provided an imaging system including the image processor apparatus and the X-ray scanner, in particular an X-ray scanner of the C-arm type.

According to one embodiment the imager includes a rotational X-ray source capable of assuming the two different angular positions.

According to one embodiment imager includes a fixed X-ray source having a movable focal point capable of assuming any one of the two different angular positions.

According to one embodiment the imager includes an X-ray tube of the double focal spot type. A double focal spot X-ray tubes allow to acquire without change of gantry or C-arm geometry or position, a set of two images from slightly different view positions

BRIEF DESCRIPTION OF THE DRAWINGS

Exemplary embodiments of the invention will now be described with reference to the following drawings wherein.

DETAILED DESCRIPTION OF EMBODIMENTS

Figure 1:
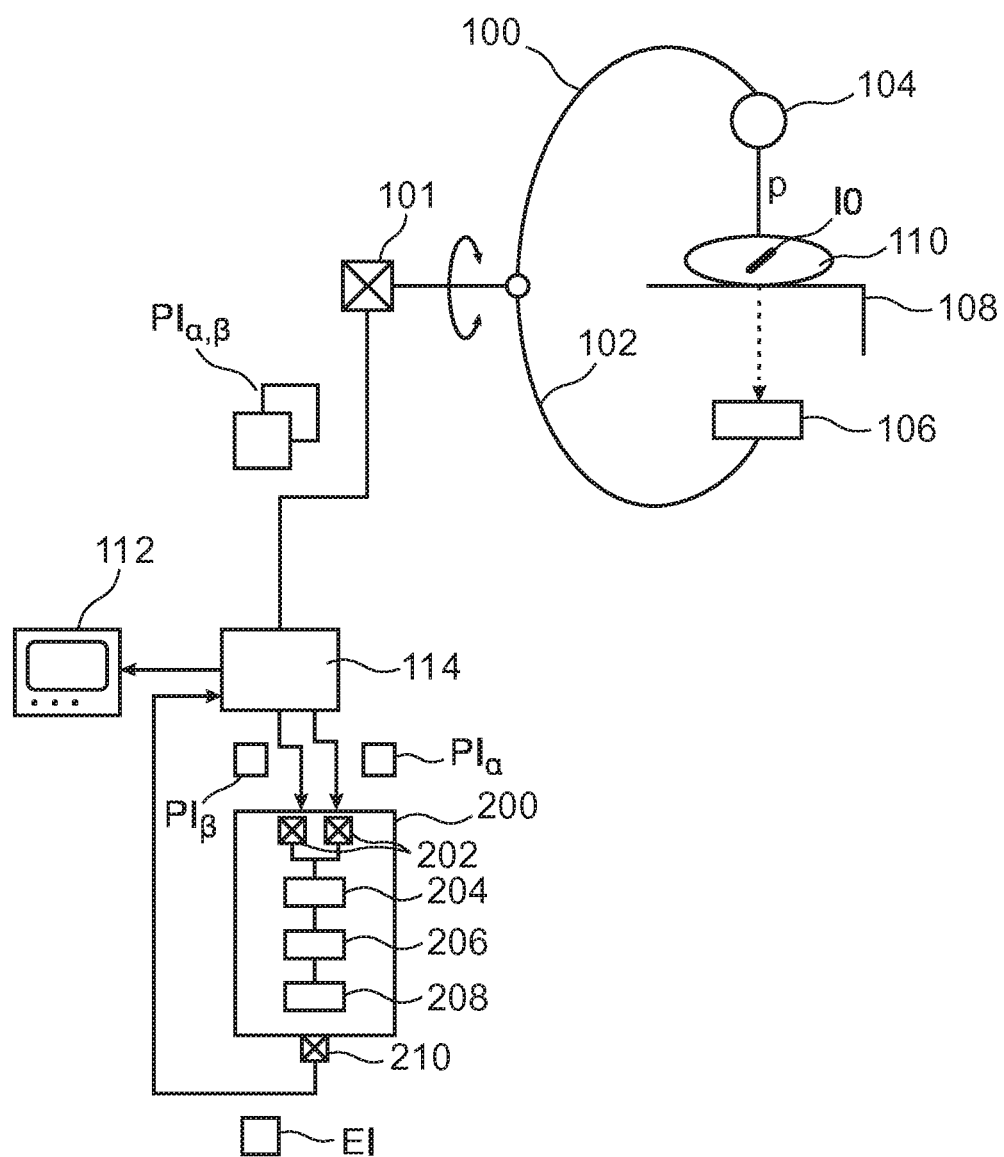
FIG. 1 shows a schematic block diagram of an imaging system including an image processor.

With reference to FIG. 1, there is shown an x-ray imager 100 of the C-arm type. X-ray imager 100 is used to acquire at least two projection images $PI_\alpha$, $PI_\beta$ of a patient 110 who is supported by an examination table 108.

Imager 100 comprises a rigid C-arm structure 102 journaled on a bearing. Journaling allows rotation of C-arm 102 around a first axis passing through journaling.

C-arm structure 102 can thus be positioned at various rotation angles α around patient 110.

C-arm 102 carries at one of its ends an x-ray source 104 and at the other end a detector 106 in opposed spatial relationship to x-ray source 104. Detector 106 includes an array of detector cells (not shown).

X-rays are emitted from x-ray source 104. The X-rays pass through patient's body 110 and are then detected at detector 120. The X-rays are formed from as an X-ray pencil beam p.

Each x-ray beam p is attenuated as it passes through the patient and impact on same. It is this attenuated x-ray beam that is detected at detector 106.

The angle of incidence ("projection direction" or "view") at which the x-ray beam impacts patient's body is partly defined by the position of C-arm 106 when the image is acquired. The degree of attenuation experienced by each individual x-ray beam p depends on the type and amount of tissue the ray p is passing through. Each attenuated x-ray beam p impinges on a detector cell and generates there an electric signal anti-proportional to the degree of attenuation.

The electric signal generated at each detector cell for x-ray beam p impinging thereon is then translated via data acquisition device 105 into a pixel value encoding a corresponding grey value. The grey values vary with the amount of attenuation experienced at the respective detector cell. Pixels that represent high attenuation portions are may encode darker shades than pixels representing low attenuation portions. The pixel values are then stored in a matrix structure forming the projection images $PI_\alpha$, $PI_\beta$.

In one embodiment X-ray tube 104 is of the double focal spot type so that it allows from the same C-arm (or, as the case may be, gantry) position to acquire at least two projection images $PI_\alpha$, $PI_\beta$, each from a different projection direction α, β.

In other embodiments X-ray tube 104 includes a single focal point which however is moveable between two positions which would likewise allow acquisition at the same C-arm position of the two projection images $PI_\alpha$, $PI_\beta$, one having its projection direction slightly off-set from the other. For present purposes it has been found that an offset angle between views α and β proves sufficient. In yet another embodiment however the x-ray tube 104 is a conventional one in which case C-arm or gantry will be moved into successively different angular positions to acquire the two projection images $PI_\alpha$, $PI_\beta$. Preferably the system allows an angular resolution of about $\Delta \geq 1.5°$. The projection angles α, β are related to the angular C-arm position which itself defined by one or more angular values.

Once the projection images $PI_\alpha$ and $PI_\beta$ are acquired they are transmitted via a suitable communication network to a workstation 114. Workstation 114 includes control software to control overall operation of imager 100 and includes console to receive instructions from a human operator. Acquired projection images $PI_\alpha$ and $PI_\beta$ can then be stored in storage either on the workstation 114 or can be stored in an external data base (not shown) for later retrieval. The projection images $PI_\alpha$, $PI_\beta$ may be stored in the DICOM format. The DICOM format includes meta-data encoding for each projection image the projection direction at which it was acquired along with its acquisition time t. Workstation 114 may also run suitable rendering software which allows viewing the images on a screen 112.

Workstation 114 is in communication with an image processor 200.

Image processor 200 includes suitable interfaces means 202 to receive copies of the two images $PI_\alpha$ and $PI_\beta$ or the images forwarded direct after their acquisition to image processor 200. Image processor 200 further includes a footprint detector 204, an image depth resolver 206 and an image manipulator 208. There is also an output interface means 210 through which an enhanced image EI based on the two received projection images $PI_\alpha$ and $PI_\beta$ can be output for further processing or for storage on workstation 114 or the external database.

In FIG. 1 the components of image processor 200 are shown as arranged in a distributed architecture and connected in a suitable communication network. The components may also be arranged as dedicated FPGAs or as hardwired standalone chips. However, this is an exemplary embodiment only. The components may also be resident on work station 140 as executable software routines. The components may be programmed in a suitable scientific computing platform such as Matlab® or Simulink® and then translated into a lower language such as C++ or C routines maintained in a library and linked when called on by work station 140.

Figure 2:
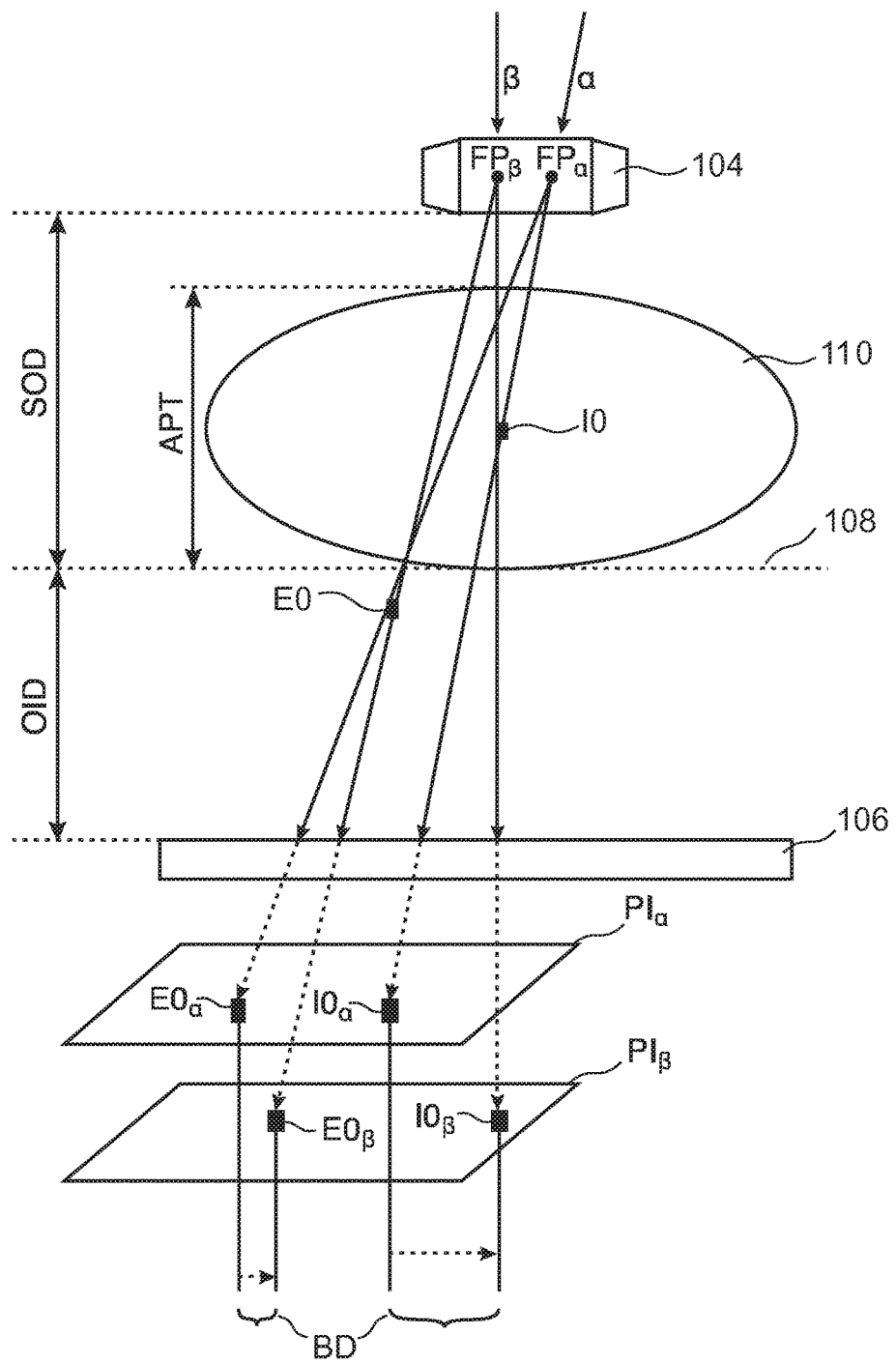
FIG. 2 shows a more detailed view of the imaging system of FIG. 1.

FIG. 2 shows in more detailed operation of x-ray tube 104 during image acquisition. Two objects are shown, an object IO internal to the patient 110's body and an object EO external to the patient's body. Internal object IO may for example be part of patient's rib and outside object EO may be part of a cable run under patent support 108 or other wiring of either the x-ray imager or other medical devices that happens to be used during intervention.

For each focal point $FP_\alpha$ and $FP_\beta$ there are schematically shown their respective x-ray beams emanating from either one and then passing through patient 110's body. Afterwards the attenuated beams impinge on detector 106's cells (not shown) thereby generating the two projection images $PI_\alpha$, $PI_\beta$. Image $PI_\alpha$ is generated by beams originating from focus point $FP_\alpha$ and image $PI_\beta$ is generated by beams originating from focus point $FP_\beta$. $EO_\alpha$, $IO_\alpha$ show footprints in Image $PI_\alpha$ of external object EO and internal object IO, respectively. Similarly, projection image $PI_\beta$ includes footprints $EO_\beta$ and $IO_\beta$ of external object EO and internal object IO, respectively.

Image processor 200 has memory stored therein a user-adjustable target range APT measured in a suitable length unit. Per default the target range APT corresponds to an average patient thickness as indicated in FIG. 2. A suitable one-dimensional reference frame is defined by measuring the APT from the upper surface of patient support to lower surface of X-ray emitter 104 but other reference frames are also contemplated. Other in-memory values which are likewise adjustable are the source-to-object-distance SOD and the object-to-image-receptor distance OID and the related source-to-image-receptor distance SID=SOD+OID. The collection of these values APT, SOD, OID along with the projection angles, that is, the C-arm position, used for each image acquisition together form the "imaging geometry" for the respective image and scanner. The target range APT is seen to be less than the SOD. Because internal object IO is within the patient's body 110, internal object IO's vertical position is within the APT. Because the imaging geometry parameters are user-definable and adjustable, apparatus 200 may also be used with different scanner types having different geometries.

In the example shown in FIG. 2, internal object IO is positioned closer to the x-ray tube 104 than is external object EO. Because of this difference in proximity, there is a length difference in binocular disparity BD of the two objects: binocular disparity BD is larger for the internal object IO because it is closer to the x-ray tube 104 than for the external object EO which is further away from the source. In other words, the BD is a measure for the depth or vertical position within the SID. Binocular disparity BD can be quantized by measuring in a suitable length unit the apparent shift of footprints $EO_\alpha$ and $EO_\beta$ of external object EO across the two images $PI_\alpha$, $PI_\beta$. The apparent shift is measurable if the two projection images $PI_\alpha$ and $PI_\beta$ are properly aligned along a common coordinate axis or are superimposed on each other. The situation is analogous for the footprints $IO_\alpha$, $IO_\beta$ of internal object IO which likewise appear to be shifted when the two image are aligned. The amount of shift, that is the binocular disparity BD, is different for the two objects IO, EO because of their different proximity to source 104 as shown in FIG. 2 and as explained above. Of course a similar consideration would hold true if external object would be positioned above the patient in which case the external object would be closer to x-ray tube 104 than internal object IO.

Broadly speaking, image apparatus 200 affords an image-depth adapted image correction by removing out-of-depth range footprints $EO_{\beta,\alpha}$ from the projection images which stem from external objects. Depth range is the user definable APT. External objects' footprints may distract the operator's attention when examining the images so a removal is desirable. The operator can then focus on the medically or anatomically relevant parts of the projection images. Apparatus 200 implements the steps of potential target objects detection in the projection images $PI_\alpha$ and $PI_\beta$. Perspective image depth of potential target objects IO, EO are then calculated based on respective footprints $EI_{\alpha,\beta}$ and $IO_{\alpha,\beta}$. Based on different binocular disparity BD of the footprints, objects EO, IO are then classified into outside objects or inside objects. One or both of the projection images $PI_{\alpha,\beta}$ are then undergoing virtual image cleaning by removing the footprints $EO_\alpha$ and/or $EO_\beta$ of the identified outside object EO.

Operation of image processing apparatus 200 will now be explained in more detail.

Operation

The two projection images $PI_{\alpha,\beta}$ acquired at slightly diverging projection directions α, β are received at interface 202 of image processor 200.

Footprint detector 204 detects footprints $EO_{\alpha,\beta}$ and $IO_{\alpha,\beta}$ either in one or both of the images as potential target objects. To achieve this, footprint detector 204 uses image segmentation techniques based on segmentation parameters such as intensity and/or gradient thresholding. The segmentation parameters specify the image portions of the images which are considered to be of potential interest. According to one embodiment the segmentation parameters can be adjusted. Intensity gradients and shape may be combined into a score value. Segments or image portions achieving a higher score are then flagged up as of potential interest. According to one embodiment, image detector 204 is configured to issue higher scores for high contrast objects. In other words, footprint detector serves as a filter to select from among the potential large numbers of segments the ones that are likely to disturb the viewer because they originate from high attenuating/high intensity objects. The segmentation parameters are for each footprint are then consolidated into footprint information.

The footprint information gathered by footprint detector 202 is then passed on to image depth resolver 260. The information on the footprints may be provided as a binary mask or a list including the co-ordinates, that is, a line and column of a pixel that has been identified or detected by footprint detector 204 to form part of a potential target object. Binary mask is a matrix having the same rows and columns as the projection images but including entries of either "0" or "1". "1" indicates that the pixel at the respective position is a part of a potential target object whereas zero indicates that it is not.

Graphic resolver 206 then uses registration or optical flow techniques to register the two projection images $PI_{\alpha,\beta}$ onto each other. A correspondence (for example based on a shape similarity measure) between footprints of across the two images $PI_{\alpha,\beta}$ are then established resulting in matched up pairs of footprints. In the example of FIG. 2, the two footprints $EO_{\alpha,\beta}$ of external objects form a matched up pair and the two footprints $IO_{\alpha,\beta}$ of the internal objects form a matched up pair. At this stage it is still not known whether the footprints relate to external or internal objects IO. This matching up of corresponding footprint pairs across the two projection images $PI_{\alpha,\beta}$ can be achieved by using SIFT techniques as described in Cheung, W., Hamarneh, G.: n-sift: n-dimensional scale invariant feature transform. Trans. Img. Proc. 18, 2012 {2021 (September 2009). Once the correspondence between the footprints are established the apparent relative shift across a common image plane of the two footprints in each pair can be measured and recorded as the measure for the binocular disparity BD for each pair. The binocular disparity BD expressed in pixels is then translated into a length unit commensurable with the length units used for the imaging geometry parameters. Image depth resolver 206 can then use the established binocular disparity BD together with the imaging parameters used by the imager when acquiring the images to calculate the vertical distance of external object EO and internal object IO within the SID range. Given detector 106 affords a resolution of about 150 μm and ≈Δ about 1° may achieve a depth resolution in vertical ATP direction of about 2 mm per pixel shift in the image plane.

Using the calculated vertical position and then comparing said position with the target range APT, footprints $EO_{\alpha, \beta}$ and $IO_{\alpha, \beta}$ can then be classified as either outside objects or inside objects, respectively. The above classification in external/outside or internal/inside objects is based on the target range APT which can be adjusted by the user during operation of apparatus 200 to so interactively define a depth value threshold and so gauge and find the optimal value for same in the circumstances. This "swinging" to and fro of the target range value to re-define the depth value threshold is useful when the object is an "interface" or "borderline" object, for example a wire lying on patient's chest. The user can set the threshold value until image depth resolver 260 recognizes the interface object as an external object. It is understood that upon receipt of a user request to change (that is shifting or enlarging) the target range, the image depth resolver re-calculates the depth value for each object thus classified to so update the candidate list of internal and external objects. This functionality of affords to the user more control on what the system will considers as internal or external objects. According to another embodiment, imager 200 automatically determines the target range APT by querying the imaging geometry parameters that were used when the projection images $PI_{\alpha, \beta}$ were acquired. The imaging geometry parameters may be obtained from the image meta-data (stored in header file) or by querying image protocol logs held in the workstation 120 or a database.

Binary masks identifying the external object footprints $EO_{\alpha,\beta}$ in one or both projection image $PI_\alpha$ or $PI_\beta$ or are then forwarded to image manipulator 208. The binary masks records pixels having been established by image depth resolver 204 to form part of external objects $EO_{\alpha,\beta}$. The image manipulator then uses this localization information to target image cleansing by virtually replacing or removing pixel information in respective external object footprints $EO_{\alpha,\beta}$ to so produce the output enhanced image EI which, when viewed, no longer shows the footprints of outside objects.

According to one embodiment image manipulator 208 uses smooth interpolation. This approach is the preferred one for image object having a relatively small dimension in at least one direction, for example, elongated structures such as wires. Pixel values inside prints $EO_{\alpha,\beta}$ are replace by interpolated pixel values interpolated from the image plane neighborhood outside the footprint. Other techniques are also contemplated for example those used for metal artifact correction or virtual bone suppression as described in Applicants' WO2011077334.

In another embodiment a piecewise constant subtraction approach is used. The piecewise constant subtraction approach is preferably used for footprints stemming from high-attenuation plate-like or sheet objects such as electrodes etc. A piecewise constant absorption contribution is subtracted in increments from the log image to eventually achieve a smooth intensity transition between outside or inside objects regions. Piecewise constant subtraction for the purpose of image cleansing is now described in more detail with reference to FIG. 3.

Figure 3:
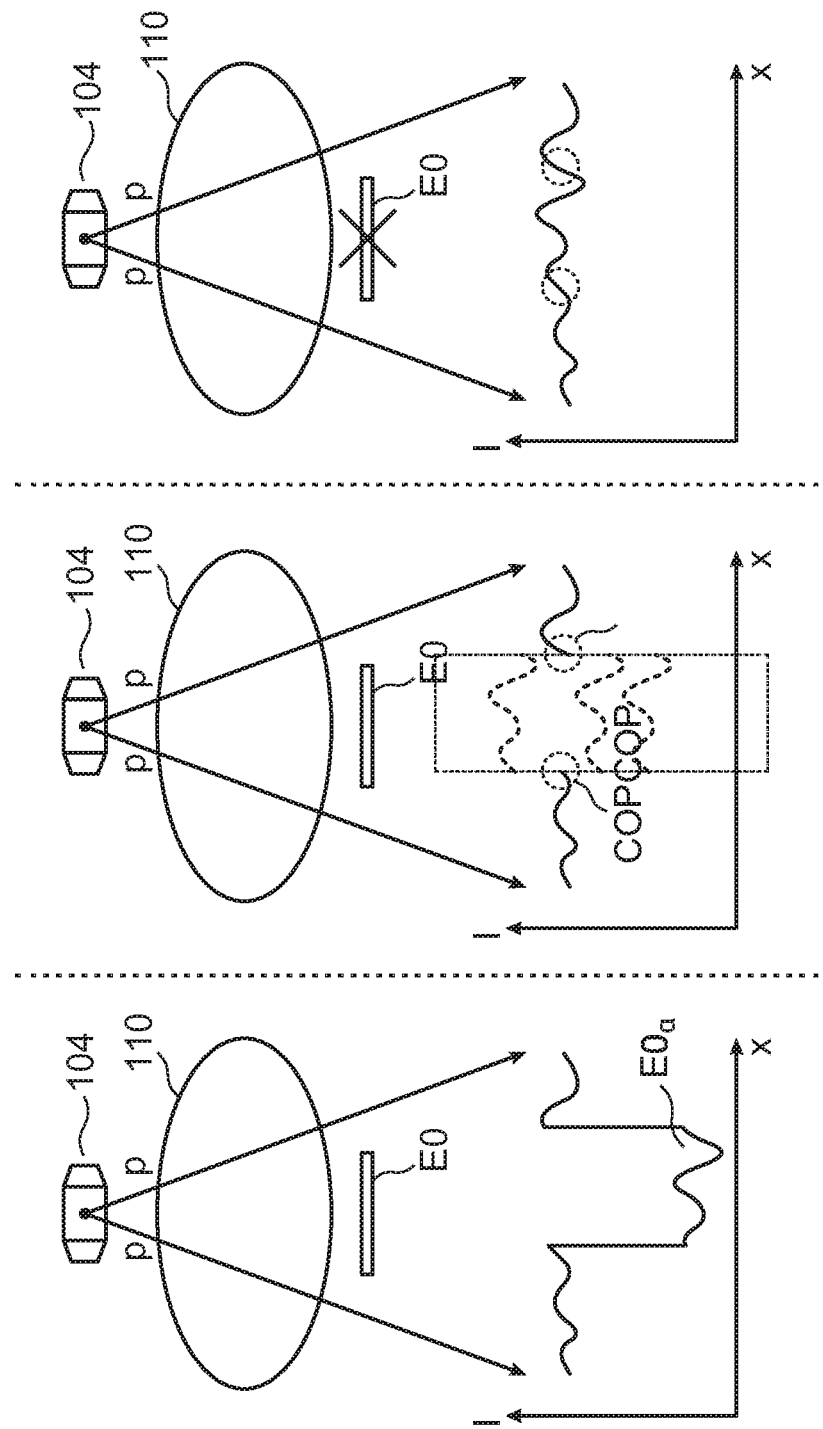
FIG. 3 shows the operation on an image of the image processor of imaging system of FIG. 1.

Left hand column in FIG. 3 shows the attenuation profile caused by external plate-like object EO. The plate-like dimension of EO causes a sharp drop in intensity at cut-off points COP because of the high attenuation caused by object EO.

Center portion of FIG. 3 shows the cut-off points COP to define the border of footprint $EO_\alpha$. Attenuation profile inside the footprint $EO_\alpha$ is shifted or successively subtracted to until a match with the cut-off points COP is detected.

Right hand side of FIG. 3 shows completion of the piece-wise constant subtraction method where the established profile is used to connect the cut-off points COP to establish a smooth transition there between. In one embodiment the attenuation profile to be fitted is effected by spline-function techniques to connect the cut-off points COP.

FIG. 3 shows a 1-dimensional cross section for clarity but is should be understood that the above is in practice carried out in the 2-dimensional image plane so the curves shown in FIG. 3 are cross-sections of the respective attenuation surfaces.

According to one embodiment a "smart" image manipulator is used that is configured to switch between the two image manipulation approaches depending on the footprint's size and/or intensity profile.

According to one embodiment image processor uses a leapfrog or by-pass functionality to boost performance. In this embodiment, the shapes, intensity profiles as established by footprint detector 204 are matched up on the fly with a database holding image footprint information of objects that are a priori known to be external object. Once the database query results in a match, the footprint information of the a priori outside object is directly passed on to image manipulator to so effect its removal. In other words, image depth resolver is leapfrogged so no image depth value for those a prior objects are calculated in this. In one embodiment a corresponding indication is issued to so alert the operator that image depth resolver has been leapfrogged. This allows operator to review the object and confirm that the decisions was correct. The by-passing is used only for shapes that are highly likely to not relate to internal objects. Elongated structures for example may not normally be allowed to by-pass the image depth resolver as it is ambiguous whether they relate to a human rib or wiring.

Figure 4:
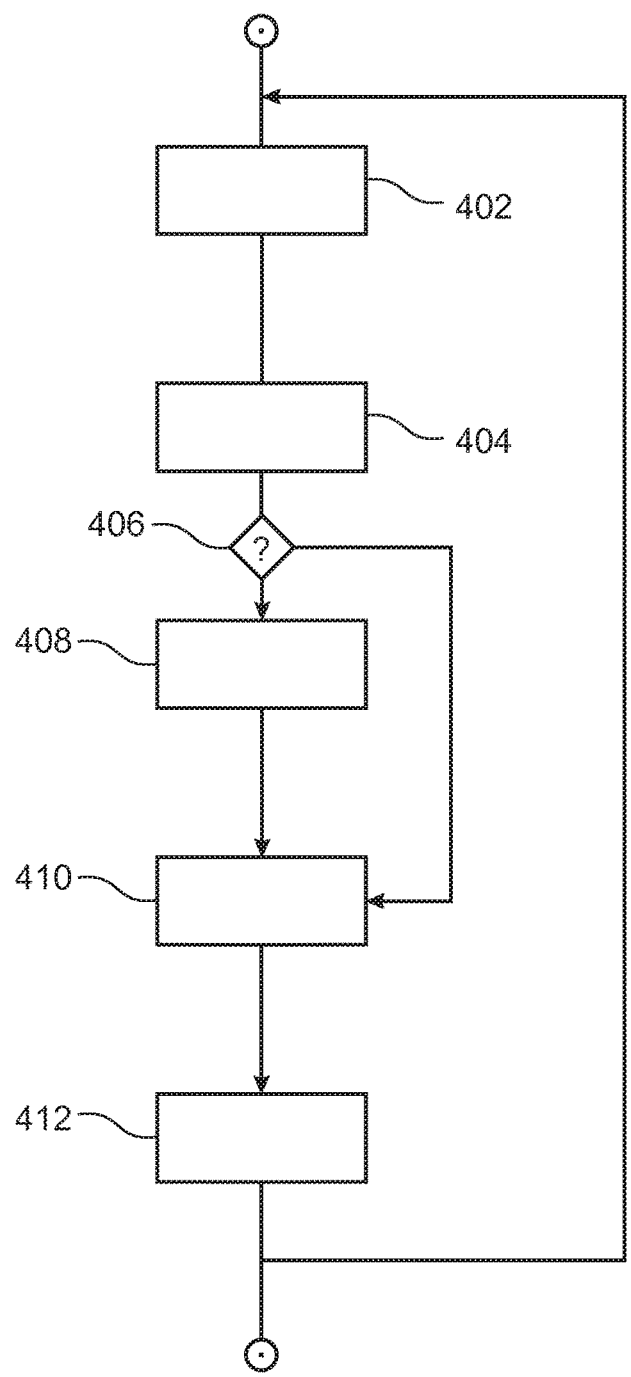
FIG. 4 is a flow chart for a method of processing an image.

The flowchart of FIG. 4 summarizes the methods for image processing.

At step 402 the projection images $PI_{\alpha,\beta}$ are received.

In step 404 footprints of potential target objects in either one or both of the projection images $PI_{\alpha,\beta}$ are established.

In step 406 the intensity profiles and/or shapes or combination thereof of the potential target footprints is compared with the database values.

If the potential target footprints are not recognized a priori to stem from objects outside objects, that is, if now the database query does not result in a match, flow control passes on to step 408 where the object depth is calculated based on binocular disparity caused by projection direction of each of the images being slightly offset.

Based on a configurable image depth threshold value defining a target range, each of the object footprints are classified into either external objects or internal objects.

The target range determines what is considered inside or outside. Object depth is either user defined or is automatically determined form the imaging geometry parameters used when the images were acquired.

At step 410 objects ("footprints") that have been classified as outside or external are then manipulated either by replacing their pixel values by new pixel information to so effect a smooth removal of the spurious object.

At step 412 the so manipulated projection image is output as an enhanced image EI.

If at step 406 it is determined that the shape or attenuation profile of the footprint matches footprint of an object that is known to be an outside object flow control can then by-pass or leapfrog the depth determination step 408 and proceed direct to step 410 where the pixel information for those a priori outside footprints are then removed.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An image processing apparatus comprising:
an input interface unit for receiving at least two projection images of a patient taken at different projection angles by an X-ray scanner, each of the images including a footprint of a target object;
an image depth resolver configured to use the two target object footprints to determine whether the target object was external to the subject when the images were taken, based on a binocular disparity between the target object footprints;
an image manipulator configured to, when the target object is determined by the resolver to be external, virtually replace at least a portion of pixel information in the respective target object footprints by different image information based on image information that is not replaced to produce an output enhanced image which, when viewed, no longer shows at least a portion of the target object footprints, and
an output interface unit configured to output the output enhanced image.

2. The apparatus of claim 1, wherein the image depth resolver is configured to establish the binocular disparity between the two target object footprints and to compare the established binocular disparity with a user definable binocular disparity threshold value to determine whether the target object is external.

3. The apparatus of claim 2, wherein the binocular disparity threshold value is adjustable in response to a user input, the value correlating to an expected or measured thickness of the subject.

4. The apparatus of claim 1, wherein the image manipulator is configured to replace the image footprint by image information interpolated from at least part of the image information forming the remainder of the at least one image.

5. The apparatus of claim 1, the apparatus further comprising an object footprint detector configured to detect the footprint in at least one of the two images.

6. The apparatus of claim 5, wherein the image depth resolver is arranged to receive input on the footprint by the object footprint detector, the object footprint detector being further configured to provide the input on the detected object footprint to the image depth resolver only if the detected object footprint matches one or more selection criteria.

7. The apparatus of claim 6, wherein the selection criteria includes any one or a combination of shape and X-ray opacity.

8. The apparatus of claim 6, wherein the object footprint detector is configured to by-pass/leapfrog the image depth resolver if, based on the one or more selection criteria, the object is a priori determined to be external.

9. An imaging system including:
an apparatus according to claim 1; and
the X-ray scanner.

10. The imaging system of claim 9,
wherein the imager includes a rotational X-ray source capable of assuming the two different angular positions or
wherein the imager includes a fixed X-ray source having a movable focal point capable of assuming any one of the two different angular positions and/or
wherein the imager includes an X-ray tube of the double focal spot type.

11. The imaging system of claim 9, wherein the X-ray scanner is of a C-arm type.

12. A computer program element for controlling an apparatus according to claim 1.

13. A computer readable medium having stored thereon the program element of claim 12.

14. A method of image processing, comprising acts of:
receiving at least two projection images of a patient taken at different projection angles by an X-ray scanner, each of the images including a footprint of a target object;
based on a binocular disparity between the two image footprints, determining whether the target object was external to the subject when the images were taken;
when the target object is determined to be external, virtually replacing at least a portion of pixel information in the respective target object footprints by different image information based on image information that is not replaced to produce an output enhanced image which, when viewed, no longer shows at least a portion of the target object footprints; and
outputting the output enhanced image.

15. A method of claim 14 further comprising:
detecting the footprints in at least one of the two images;
establishing whether the detected object footprint matches one or more selection criteria, and if yes, by-passing the determining act based on the binocular disparity and then executing the act of replacing at least the portion of pixel information in the respective target object footprints.

16. An image processing apparatus comprising:
an input interface unit for receiving at least two projection images of a patient taken at different projection angles by an X-ray scanner, each of the images including a footprint of a target object;
an image depth resolver configured to use the two target object footprints to determine whether the target object was external to the subject when the images were taken, based on a binocular disparity between the target object footprints;
an image manipulator configured to, when the target object is determined by the resolver to be external, virtually replace pixel information in the respective target object footprints by image information interpolated from at least part of the image information forming a remainder of the at least one image to produce an output enhanced image which, when viewed, no longer shows the target object footprints; and
an output interface unit configured to output the output enhanced image.

17. An image processing apparatus comprising:
an input interface unit for receiving at least two projection images of a patient taken at different projection angles by an X-ray scanner, each of the images including a footprint of a target object;
an image depth resolver configured to use the two target object footprints to determine whether the target object was external to the subject when the images were taken, based on a binocular disparity between the target object footprints;
an object footprint detector configured to detect the footprint in at least one of the two images, wherein the image depth resolver is arranged to receive input on the footprint by the object footprint detector and wherein the object footprint detector is configured to bypass/leapfrog the image depth resolver if, based on one or more selection criteria, the object is a priori determined to be external;
an image manipulator configured to, when the target object is determined by the resolver to be external, virtually replace or remove pixel information in the respective target object footprints to produce an output enhanced image which, when viewed, no longer shows the target object footprints; and
an output interface unit configured to output the output enhanced image.

18. A method of image processing, comprising acts of:
receiving at least two projection images of a patient taken at different projection angles by an X-ray scanner, each of the images including a footprint of a target object;
based on a binocular disparity between the two image footprints, determining whether the target object was external to the subject when the images were taken;
when the target object is determined to be external, virtually replacing or removing pixel information in the respective target object footprints to so produce an output enhanced image which, when viewed, no longer shows the target object footprints;
detecting the footprints in at least one of the two images;
establishing whether the detected object footprint matches one or more selection criteria, and if yes, by-passing the determining act based on the binocular disparity and then executing the act of replacing or removing the pixel information in the respective target object footprints; and
outputting the output enhanced image.

* * * * *